United States Patent [19]

Hansen

[11] Patent Number: 4,893,934
[45] Date of Patent: Jan. 16, 1990

[54] AETHALOMETER

[75] Inventor: Anthony D. Hansen, Berkeley, Calif.

[73] Assignee: The United States of America as represented by the United States Department of Energy, Washington, D.C.

[21] Appl. No.: 148,328

[22] Filed: Jan. 25, 1988

[51] Int. Cl.$^4$ ...................... G01N 21/01; G01N 21/59
[52] U.S. Cl. ...................................... 356/434; 356/38
[58] Field of Search ................ 356/38, 433, 434, 435, 356/438, 440; 250/343

[56] References Cited

U.S. PATENT DOCUMENTS

| Re. 31,232 | 5/1983 | Butera | 356/438 |
|---|---|---|---|
| 1,996,233 | 4/1935 | Darrah | 356/434 |
| 3,292,484 | 12/1966 | Clay | 356/434 |
| 3,562,795 | 2/1971 | Frenk | 356/435 |
| 3,653,773 | 4/1972 | Childs | 356/38 |
| 3,684,378 | 8/1972 | Lord | 356/434 |
| 3,730,627 | 5/1973 | Kent | 356/434 |
| 3,790,289 | 2/1974 | Schmidt | 356/434 |
| 4,027,981 | 6/1977 | Steinhatz | 356/434 |
| 4,035,086 | 7/1977 | Schoeffel et al. | 356/434 |
| 4,111,559 | 9/1978 | Smith et al. | 356/437 |
| 4,123,159 | 10/1978 | Hollander et al. | 356/38 |
| 4,543,815 | 10/1985 | Troup et al. | 356/438 |
| 4,614,434 | 9/1986 | Welch et al. | 356/434 |
| 4,640,621 | 2/1987 | Rose | 356/434 |

FOREIGN PATENT DOCUMENTS

| 2643331 | 3/1978 | Fed. Rep. of Germany | 356/434 |
|---|---|---|---|
| 658409 | 4/1979 | U.S.S.R. | 356/434 |

OTHER PUBLICATIONS

Rosen et al, "An Instrument for the Quasi-Real Time Measurement of the Optical Absorption Coefficient of Ambient Aerosols", Lawrence Berkeley Laboratory (LBID—256), Aug. 1980.

Hansen et al, "Real-Time Measurement of the Absorption Coefficient of Aerosol Particles", *Applied Optics*, vol. 21, No. 17, (1 Sep. 1982), pp. 3060-3062.

Hansen et al, "Real-Time Measurement of the Absorption Coefficient of Aerosol Particles", Lawrence Berkeley Laboratory (LBL-15298), Jul. 1983, pp. 4-7:4-10.

Hansen et al., "The Aethalometer", *The Science of the Total Environment*, vol. 36, (1984), pp. 191-196.

*Primary Examiner*—Richard A. Rosenberger
*Attorney, Agent, or Firm*—Clifton E. Clouse; Roger S. Gaither; William R. Moser

[57] ABSTRACT

An improved aethalometer (10) having a single light source (18) and a single light detector (20) and two light paths (21, 22) from the light source (18) to the light detector (20). A quartz fiber filter (13) is inserted in the device, the filter (13) having a collection area (23) in one light path (21) and a reference area (24) in the other light path (22). A gas flow path (46) through the aethalometer housing (11) allows ambient air to flow through the collection area (23) of the filter (13) so that aerosol particles can be collected on the filter. A rotating disk (31) with an opening (33) therethrough allows light for the light source (18) to pass alternately through the two light paths (21, 22). The voltage output of the detector (20) is applied to a VCO (52) and the VCO pulses for light transmission separately through the two light paths (21, 22) are counted and compared to determine the absorption coefficient of the collected aerosol particles.

5 Claims, 3 Drawing Sheets

AETHALOMETER

The United States Government has rights in this invention pursuant to Contract No. DE-AC03-76SF00098 between the U.S. Department of Energy and the University of California.

BACKGROUND OF THE INVENTION

This invention relates to optical analyzers and more particularly to an instrument for measuring the absorption coefficient of light absorbing suspensions, or black carbon in aerosol particulate material.

Recent studies have shown that large concentrations of graphitic, or black, carbon particles are found in the atmosphere in both urban and remote locations. These particles are produced in combustion and have a large absorption cross section, on the order of 10 $m^2/g$. Their presence affects radiation transfer through the atmosphere, causing visibility degradation and possible changes in the regional or global balance. The size of these effects depends critically on both the concentration of their particles and their single-scattering albedo, which is determined by the relative magnitude of the scattering and absorption coefficients. The scattering coefficient is easily measured by a nephelometer.

However, measurements of the absorption coefficient of these ambient aerosols are difficult, mainly because of the small magnitude of this coefficient: the coefficient typically being in the order of from about $10^{-3}$ to $10^{-6}$ $m^{-1}$. An instrument has been developed by the Lawrence Berkeley Laboratory, of the University of California, to determine the coefficient by measuring the attenuation of a light beam transmitted through aerosol particles that are continuously collected from the atmosphere on a suitable filter. This instrument, named an aethalometer (derived from the Greek word meaning "to blacken with soot"), has been described by A. D. A. Hansen, H. J. Rosen, and T. Novakov, in "Real-Time Measurement of the Absorption Coefficient of Aerosol Particles," Applied Optics, Vol. 21, No. 17, Sept. 1, 1982, pp. 3060 et seq.

In general, the above aethalometer uses a cellulose fiber light-transmitting filter which is partially covered by a transparent mask so that air can be drawn through only a small part of the filter on which the particles are collected. The non-collecting portion of the filter covered by the mask is used as a reference. Light from a stabilized lamp passes through a 530-nm bandpass filter and is then directed by a quartz light guide to uniformly illuminate the collecting and reference areas of the cellulose filter. The light transmitted through these two portions of the filter is picked up by two separate optical fibers set into the filter support, giving signal and reference beam intensities proportional to the magnitude of light transmitted through the two portions of the filter. The fibers conduct these beams to two separate silicon detectors whose outputs are coupled to a logarithmic ratiometer. The voltage output of this unit is proportional to the instantaneous optical attenuation due to the absorption of the collected particles. At selected time intervals, the output signal of the ratiometer is digitized and stored in a suitable computer. This result is subtracted from the previous measurement, giving a difference proportional to the average of the absorption coefficient during the averaging time interval.

The averaging time interval is primarily determined by the concentration of the aerosols in the atmosphere, since there must be sufficient particles collected in the filter during the time interval so that there is a readily detectable difference between the beginning and ending coefficient of absorption. The higher the concentration of aerosol particles, the shorter may be the averaging time interval, and vice versa.

Aethalometers as above described have been quite satisfactory when used at ground stations for measuring the absorption coefficient of aerosol particles in the atmosphere. However, they have not proven satisfactory in very rapidly changing environmental conditions such as the study of clouds of smoke rising from ground level fires. In such clouds, the concentration of black carbon particles is usually quite stratified, with the concentration varying widely at different heights from the ground. In order to make a proper study of such clouds, a plane with an on-board aethalometer should cross through the cloud at different levels, with the absorption coefficient being measured at each level. However, such clouds often have a relatively small diameter such that the flight time through the cloud is insufficient for enough particles to be collected in a single pass to enable accurate determinations of the absorption coefficient at that level to be made.

SUMMARY OF THE INVENTION

It is the primary object of the present invention to provide an improved aethalometer for measuring the absorption coefficient of graphitic aerosols which can give accurate measurements of such coefficient with considerably less amount of particles collected in a averaging time interval than heretofore possible, and such that airborne analyses of atmospheric aerosols may be carried out.

Additional objects, advantages and novel features of the invention will be set forth in the description which follows, and in part, will become apparent to those skilled in the art upon examination of the following, or may be learned by practice of the invention. The objects and advantages of the invention may be realized and attained by means of the instrumentalities and combinations pointed out in the appended claims.

The present invention lies, to a great extent, in the recognition of the reasons why the prior art aethalometer described above did not have satisfactory sensitivity for accurate measurement of absorption coefficients from very small amounts of collected black carbon particles. In particular, it was recognized that the us of two separate detectors for the collecting and reference areas of the filters requires a relatively large amount of particles to be collected to ensure meaningful measurements. Thus, even a very slight drift in the output of either of the detectors relative to the other may cause a difference in the outputs of the two detectors that will either mask or accentuate a small actual change in optical absorption. As a consequence, it is necessary in the prior aethalometer to have a relatively large amount of particles collected in the averaging time interval so that the signal from the detected change in absorption coefficient would be relatively great as compared to drift errors.

The present invention also lies in the recognition that an aethalometer must be very stable mechanically so that the light paths through the collecting and reference areas of the filter do not vary because movement of parts of the device caused by shock or vibration. Again, with very small magnitudes of change of the absorption coefficient of the collected particles, small degrees of physical changes of the light paths during measurement will introduce large errors into the measurements.

To achieve the foregoing and other objects, and in accordance with the present invention as described and broadly claimed herein, an improved aethalometer is provided having a single light source and a single detector, two light paths from the light source through the collecting and reference areas of a light transmitting filter to said detector, and shutter means for allowing light to pass alternately through the two light paths.

In further accordance with the present invention the light paths are comprised by light-transmitting solid members secured against movement relative to the housing of the aethalometer.

BRIEF DESCRIPTION OF THE DRAWINGS

The accompanying drawings which are incorporated in and form part of the application, together with the description serve to explain the principles of the invention.

DESCRIPTION OF THE PREFERRED EMBODIMENT

Figure 1:
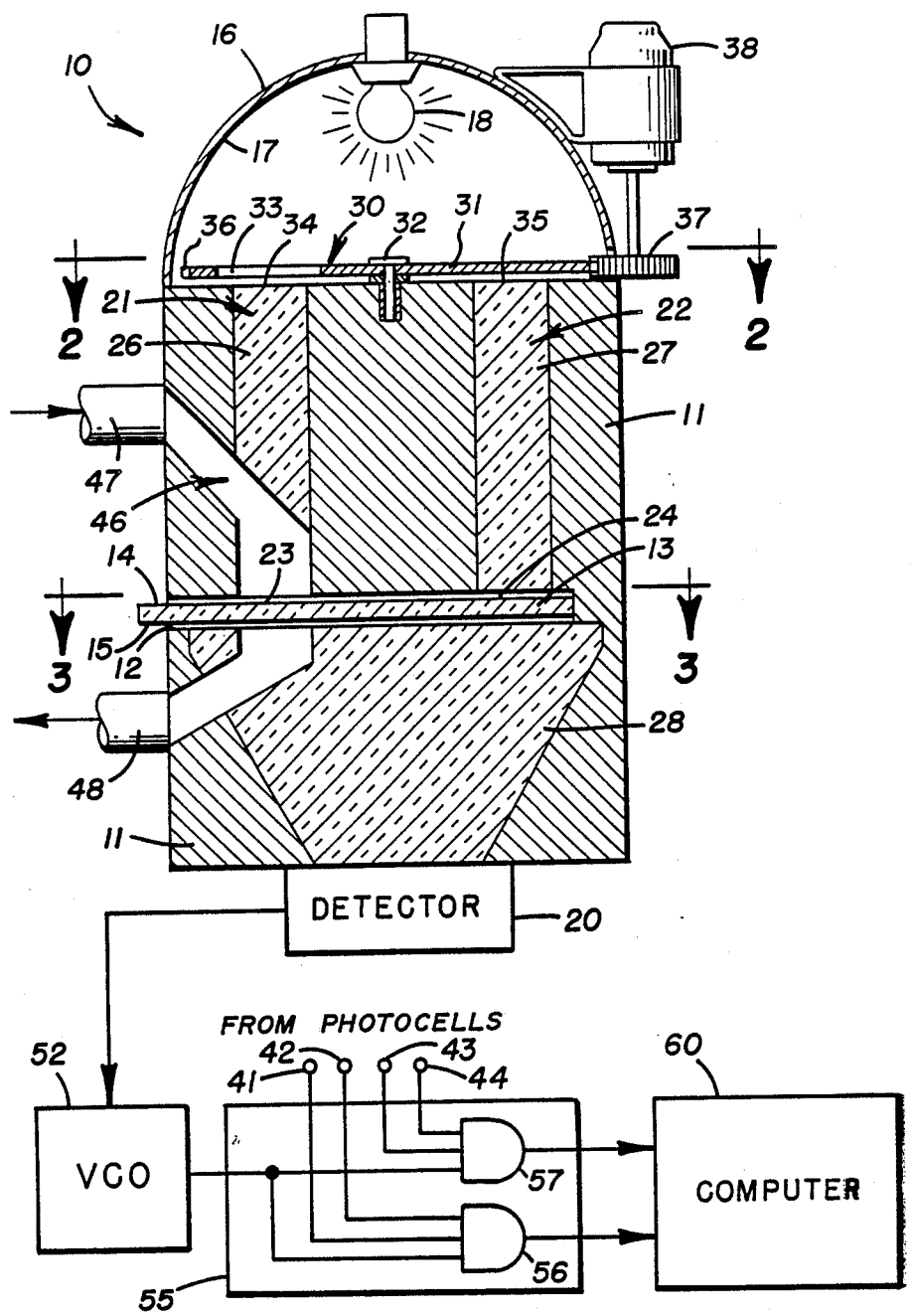
FIG. 1 shows partly in section and partly in block diagram form an improved aethalometer in accordance with the present invention.

Referring now to the drawings, wherein a preferred embodiment of the invention is illustrated, the improved aethalometer 10 includes a generally circular in cross-section, housing 11 with a radially extending slot 12 for the reception of a light-transmitting filter 13 having parallel opposed surfaces 14 and 15. The housing 11 has a dome portion 16 with a mirrored light-reflective internal surface 17. A single light source 18, such as a stabilized incandescent lamp, is mounted within the dome portion 16 and is rigidly secured against movement relative to the housing 11. Also rigidly secured against movement relative to the housing 11 is a single photoelectric light detector 20.

Two light paths 21 and 22 are provided for the transmission of light from light source 18 to the light detector 20, the light paths passing through first and second spaced apart collection and reference areas 23 and 24 of filter 13. Light paths 21 and 22 include separate light-transmitting solid members 26 and 27, preferably lucite rods, mounted securely in housing 11, to transmit light from light source 18 to the collection and reference areas 23 and 24 of filter 13. The light paths 21 and 22 also include a common light-transmitting solid member 28, again preferably of lucite, disposed between the lower surface 15 of filter 13 and the light detector 20. The solid member 28 is also mounted securely in housing 11 so that it will not move relative to the housing.

A shutter means 30 is provided for allowing light from the light source 18 to pass through the light paths 21 and 22 alternately to the collection and reference areas 23 and 24 of filter 13 while simultaneously preventing light from passing to the other of those areas. The shutter means 30 includes disk 31 mounted in the dome 16 for rotation about a central axis 32. The disk 31 preferably has a black matte finish to prevent reflection and has an opening 33 therethrough to allow light from the light source 18 to impinge upon the ends 34 and 35 of the lucite rods 26 and 27. The periphery of disk 31 is provided with gear teeth 36 for meshing engagement with the motor driven spur gear 37. The motor 38 preferably drives the disk 31 at a speed of about 3.5 seconds per revolution.

Figure 2:
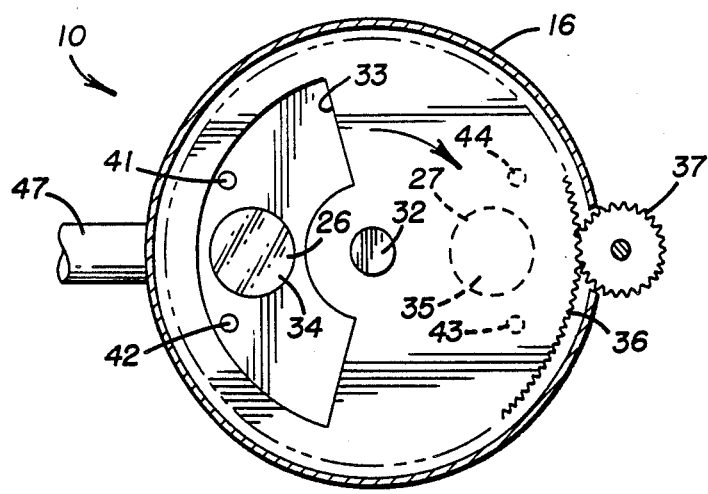
FIGS. 2 and 3 are sectional views of the improved aethalometer of FIG. 1, taken on lines 2—2 and 3—3 thereof.
Figure 3:
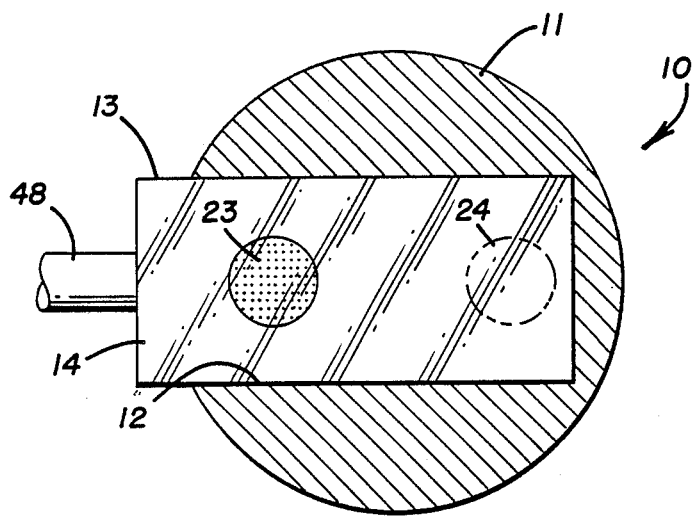

As best seen in FIG. 2, two photocells 41 and 42 are mounted in housing 11 adjacent the upper end 34 of lucite rod 26 so that they may be illuminated by the light source 18 through the opening 33 of disk 31. In particular, photocell 40 is mounted relative to lucite rod 26 so that photocell 40 is illuminated and energized at a time after the upper end of lucite rod 26 has become fully exposed through the disk opening 33 to the light source 18. Photocell 41 is mounted relative to lucite rod 26 so that photocell 41 is blocked from light source 18 and de-energized at a time while the upper end of lucite rod is still fully exposed through the disk opening 33 to the light source 18. Photocells 43 and 44 are similarly mounted with respect to the upper end 35 of lucite rod 27.

In order to monitor a gas having light absorbing black carbon in aerosol particulate form, the aethalometer 10 has a flow path 46 through the housing, the flow path being connected to inlet and outlet conduits 47 and 48 for flow of such gas through the collection area 23 of filter 13.

In use, the aethalometer 10 is first zero calibrated by inserting a clean filter 13 in housing slot 12 and turning on the light source 18 and motor 38. As the motor driven disk 31 rotates, the ends of the lucite rods 26 and 27 will be alternately exposed to the light source 18 so that light will be alternately transmitted through the collection and reference areas 23 and 24 to the detector 20. The output of the detector 20 will be a analog voltage signal proportional to the intensity of the light received by the detector and such signal is then applied to the input of a voltage controlled oscillator (VCO) 52. The VCO output will be a series of digital pulses at a frequency proportional to the applied voltage from the detector, and thus proportional to the degree of transmission through the collection and reference areas of the filter.

The output pulse signals of the VCO 52 are then applied to the logic circuit 55, shown herein for simplicity as comprised by two AND gates 56 and 57. The VCO signals and the outputs from the two timing photocells 41 and 42 are all applied to AND gate 56 whose output will be a series of pulses for a predetermined period during which both photocells 41 and 42 are concurrently illuminated. During this period of time the lucite rod 26 will be fully exposed to the light source 18, with no shadow from the disk 31 falling on the rod 26. The length of this period of time is determined by the arcuate length of the disk opening 33 and the rotational speed of the disk. With a rotational speed of about 3.5 seconds per revolution, the time period during which both photocells 41 and 42 will be illuminated is preferably in the order of 1.0 seconds.

As the disk 31 continues to rotate, photocells 43 and 44 will both be concurrently illuminated and energized for a period of time equal to that above so that AND gate 57 will pass the VCO pulses generated while the lucite rod 27 is fully exposed to the light source 18.

Figure 4:
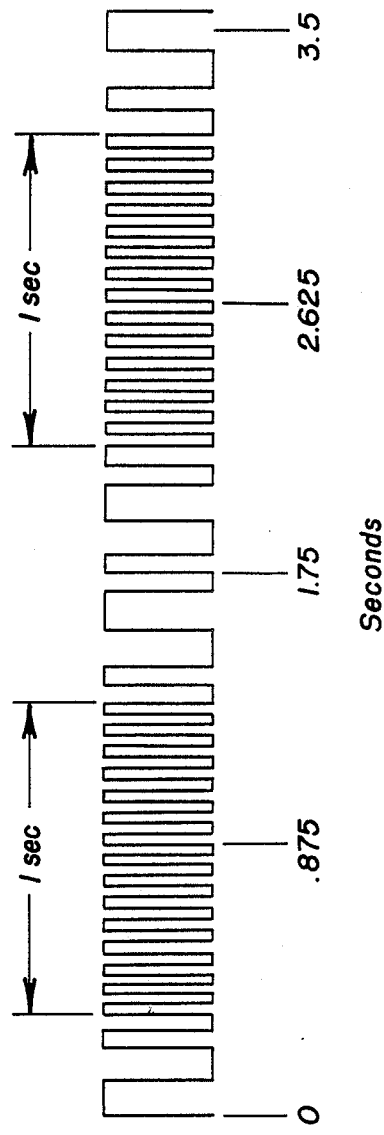
FIGS. 4 and 5 illustrate outputs from the detector and voltage controlled oscillator and from the logic circuit.

The outputs of the VCO 52 and the logic circuit 55 are illustrated in FIG. 4. During the time that the photocells 41 and 42 are concurrently illuminated, the frequency of the output signal from the VCO will be steady. Then, as the disk rotates and begins to obscure the end of lucite rod 26, the VCO frequency will decrease. Continued rotation of the disk can cause the disk opening 33 to begin to expose rod 27 before rod 26 is completely cut off from the light, so that the combined transmission of light through the two light paths may cause the VCO output to increase and then decrease when the rod 26 is full cut off. The light transmitted through rod 27 will increase as the end of the rod becomes more fully exposed. During the time of full exposure, i.e., when photocells 43 and 44 are both concurrently illuminated, the VCO output will again be steady.

Figure 5:
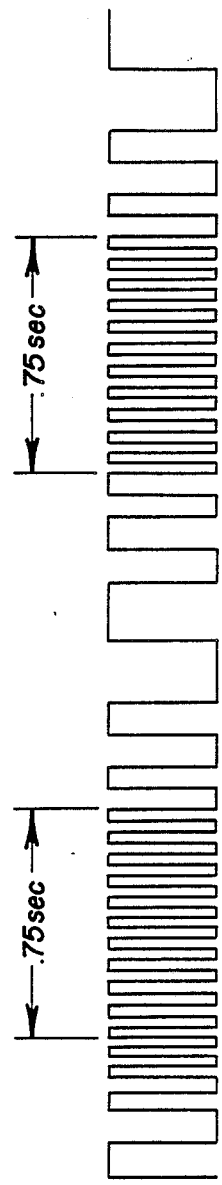

If desired, the arcuate length of the disk opening 33 may be reduced so that one of the lucite rods is fully cut off from the light source before the other rod begins to be illuminated. The outputs of the VCO and the AND gates for such an arrangement is shown in FIG. 5. Since the disk opening 33 is less in length, the time that the two photocells in each set are both illuminated will be shorter than previously described. During the time both light paths are fully cut off from the light source, the output from the VCO will have a minimum frequency.

In either event the only steady outputs from the logic circuit 55 are then fed to computer 60, wherein the number of pulses from each of the AND gates 56 and 57 are separately counted, with the counts being proportional to the degree of light transmission through the two collection and reference areas of the filter. The absolute amount of transmission through each of the two light paths will differ because, for example, the light path 21 will include part of the gas flow path 46 while light path 22 does not. However, the physical parameters of the two light paths will remain constant so that there will be a constant resulting difference in the counts representing light transmission through the collection and reference areas of the filter.

The aethalometer can then be calibrated by inserting a filter having an accumulation of aerosol particles on the collection area with a known absorption coefficient. The aethalometer is then operated to obtain pulse counts through the collection and reference areas with the difference in count (adjusted for zero calibration) being indicative of the known absorption coefficient.

In airborne analyses, the aethalometer is carried in an airplane with suitable apparatus (not shown) for opening and closing conduit 47 and for allowing outside atmospheric air to flow through the flow path 46 at a controlled rate. The airplane is then flown, at a desired elevation, into the cloud under study, and conduit 47 is opened to allow the outside atmosphere to pass through the flow path 46 so that the black carbon particulate matter will collect on the filter 13. With a cycle time of 3½ seconds, the computer will determine from the pulse counts from logic circuit 55 the degree of increase of collected black carbon particles from the previous cycle and the consequent absorption coefficient for the particles collected in the cycle. As the plane leaves the cloud, the conduit 47 is closed and the plane proceeds to the next elevation. Runs through the cloud are repeated until the desired amount of data is accumulated. The disclosed aethalometer is specific to the determination of concentrations of black carbon particles. Other aerosols, such as ammonium sulfate, ammonium nitrate, mineral dust, hydrated salts and so forth, may cause atmospheric turbidity but will not affect the measuring of the absorption coefficient of the black carbon particles by the present apparatus.

With the use of a single detector and a mechanically stable construction, the present aethalometer provides much greater sensitivity and accuracy than the previous device. Low concentrations of aerosol particles, which would require about four minutes to increase with the previous device can now be measured in slightly over three seconds. This significant improvement permits airborne analyses to be carried out which were impossible with the prior apparatus.

The described device has a number of additional advantages. For example, the filter 13 should preferably be made of prefired quartz fibers so that the collected particles may be easily chemically analyzed after removal from the aethalometer.

Also, the sampling period of the instrument can be changed by simply changing the speed of the motor 38. Thus, if the aerosol concentration is sufficiently high that measurable amounts of particles are collected in less than 3½ seconds, the speed of the motor can be increased so that sequential measurements are taken in shorter periods of time. Likewise, the speed of the motor can be reduced to provide a larger collection time per cycle of operation. With the disclosed photocell arrangement, the duration of the outputs of the logic circuit 55 will be automatically adjusted so that the outputs are only taken when the lucite rods 26 and 27 are fully exposed to light.

If desired, the aethalometer 10, with its VCO 52 and logic circuit 55 can be at one location while the computer 60 can be at a remote site. In such case, suitable equipment would be used to transmit the signals to the computer for counting and analysis.

The foregoing description of the preferred embodiment has been presented for the purposes of illustration and description. It is not intended to be exhaustive or to limit the invention to the precise features described, and obviously many modifications and variations are possible in light of the above teaching. The embodiment was shown in order to explain most clearly the principles of the invention and the practical applications thereby to enable others in the art to utilize most effectively the invention in various other modifications as may be suited to the particular use contemplated. It is intended that the scope of the invention be defined by the claims appended hereto.

What is claimed is:

1. An improved aethalometer comprising:
   a housing having a slot for the reception of a light transmitting filter,
   a single light source secured against movement relative to said housing,
   a single light detector secured against movement relative to said housing,
   means forming first and second light paths through said housing for the transmission of light from said light source to said light detector, said first and second light paths passing through first and second separate areas of a filter disposed in said slot, said means including first and second separate solid light-transmitting solid members disposed in said first and second light paths respectively between said light source and said slot, said first and second solid members each having an end disposed for reception of light from said light source,
   shutter means for allowing light from said light source to pass alternately through said light paths and alternately solely through one of said first and second areas of a filter disposed in said slot while completely blocking light from said light source from passing through the other of said first and second areas of said filter, said shutter means including an opaque member disposed between said light source and said ends of said first and second light-transmitting solid members said opaque member having an opening therethrough, and means for moving said opaque member in a path of movement between a first position wherein said end of said first light-transmitting solid member is completely exposed through said opening to light from said light source and said end of said second light-transmitting solid member is completely blocked from said light, and a second position wherein the exposure and blocking of said ends of said light-transmitting solid members is reversed, a first pair of photocells associated with said end of said first light-transmitting solid member, said photocells being fixed to said housing and on opposite sides of said first solid member end along said path of movement of said opaque member, a second pair of photocells associated with said end of said second light-transmitting solid member, said photocells being fixed to said housing and on opposite sides of said second solid member end along said path of movement of said opaque member, said opening of said opaque member being greater in size than either of said ends of said first or second light-transmitting solid members and the photocells associated therewith, means forming a flow path for passage of gas through said housing, said flow path allowing gas to pass through one only of said first and second areas of a filter disposed in said slot, a single generating means for generating signals proportional to the magnitude of light received by said light detector, logic means for alternately outputting said signals during the time while light from said light source is passing through said opening of said opaque member simultaneously to said end of said first light-transmitting solid member and both of said first pair of photocells, and then during the time while light is passing through said opening of said opaque member simultaneously to said end of said second light-transmitting solid member and both of said second pair of photocells.

2. An improved aethalometer as set forth in claim 1, wherein said means forming first and second light paths includes a single light-transmitting solid member disposed in said housing between said slot and said light detector and said light detector and in both of said first and second light paths, said single light-transmitting member being secured against movement relative to said housing.

3. An improved aethalometer as set forth in claim 1, and further including a quartz fiber filter disposed in said slot, said filter having parallel opposed surfaces.

4. An improved aethalometer as set forth in claim 1, wherein said single generating means includes a voltage controlled oscillator connected to said light detector for generating signals having a frequency proportional to the magnitude of light received by said light detector.

5. An improved aethalometer as set forth in claim 1, wherein said opaque member is a rotatable disk, wherein said path of movement is circular, and wherein said means of moving said opaque member is a motor.

* * * * *